United States Patent [19]

Bauer et al.

[11] 4,259,518
[45] Mar. 31, 1981

[54] 3-METHYL-5-KETO-α,ω-ALKENEDIOIC ACIDS AND ESTERS

[75] Inventors: Kurt Bauer, Holzminden; Detlef Hagena, Hoexter, both of Fed. Rep. of Germany

[73] Assignee: Bayer Aktiengesellschaft, Leverkusen, Fed. Rep. of Germany

[21] Appl. No.: 71,431

[22] Filed: Aug. 30, 1979

[30] Foreign Application Priority Data

May 26, 1979 [DE] Fed. Rep. of Germany ........ 2921430

[51] Int. Cl.³ .................... C07C 59/76; C07C 69/738
[52] U.S. Cl. ................. 560/176; 252/522 R; 562/578; 568/346; 568/356; 568/375
[58] Field of Search ........................ 562/578; 560/176

[56] References Cited

U.S. PATENT DOCUMENTS 2,436,536  2/1948  Singleton .......................... 562/578
3,383,412  5/1968  Wellman et al. .................... 562/578

FOREIGN PATENT DOCUMENTS 1282644  11/1968  Fed. Rep. of Germany .......... 560/176

*Primary Examiner*—Vivian Garner
*Attorney, Agent, or Firm*—Sprung, Felfe, Horn, Lynch & Kramer

[57] ABSTRACT

The invention concerns new 3-methyl-5-keto-α,ω-alkene-dioic acids of the general formula

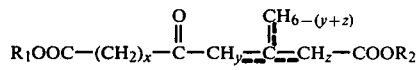

wherein
the double bond is in one of the positions indicated by the broken lines,
$R_1$ and $R_2$ independently of one another are a hydrogen atom or a $C_1$-$C_4$-alkyl group,
x is an integer from 9 to 11 and
y and z independently of one another are 1 or 2, but cannot both be 1;

a process for their preparation and their use for the preparation of macrocyclic β-methyl ketones which are valuable fragrances.

2 Claims, No Drawings

3-METHYL-5-KETO-α,ω-ALKENEDIOIC ACIDS AND ESTERS

The invention relates to 3-methyl-5-keto-α,ω-alkenedioic acids of the general formula

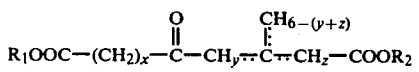

in which
the double bond is in one of the positions indicated by the broken lines,
$R_1$ and $R_2$ independently of one another represent a hydrogen atom or a $C_1$-$C_4$-alkyl group,
x denotes an integer from 9 to 11 and
y and z independently of one another are 1 or 2, but cannot both be 1.

The invention further relates to a process for the preparation of the compounds of the general formula (I). The process is characterized in that an α,ω-alkanedioic acid derivative of the general formula

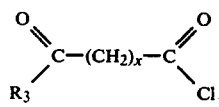

in which
x has the meaning given under formula (I) and
$R_3$ represents chlorine or a $C_1$-$C_4$-alkoxy group is reacted with a dimethylacrylic acid derivative of the general formula

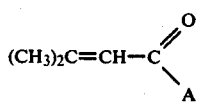

in which
A represents chlorine, a $C_1$-$C_4$-alkoxy radical or the β,β-dimethylacryloyloxy radical in the presence of a Lewis acid.

The invention further relates to the use of the 3-methyl-5-keto-α,ω-alkenedioic acids according to the invention, of the formula (I), for the preparation of macrocyclic β-methyl-ketones.

The following may be mentioned as examples of the compounds according to the invention, of the formula (I): 3-methyl-5-keto-pentadecene-2-dioic acid, 3-methyl-5-keto-pentadecene-3-dioic acid, 3-methylene-5-keto-pentadecanedioic acid, 3-methyl-5-keto-hexadecene-2-dioic acid, 3-methyl-5-keto-hexadecene-3-dioic acid, 3-methylene-5-keto-hexadecanedioic acid, 3-methyl-5-keto-heptadecene-2-dioic acid, 3-methyl-5-keto-heptadecene-3-dioic acid, 3-methylene-5-keto-heptadecanedioic acid, and the monomethylesters, the dimethyl esters, the monoethyl esters and the diethyl esters of the said acids.

The following may be mentioned as examples of the compounds of the formula (II): the dichlorides of α,ω-undecanedioic acid, α,ω-dodecanedioic acid and α,ω-tridecanedioic acid, and, as preferred compounds, the monoalkyl ester chlorides, especially the monomethyl ester chlorides and monoethyl ester chlorides, of α,ω-undecanedioic acid, α,ω-dodecanedioic acid and α,ω-tridecanedioic acid.

Preferred examples of the compounds of the formula (III) are the $C_1$-$C_4$-alkyl esters of dimethylacrylic acid, such as the methyl, ethyl, propyl, isopropyl, n-butyl and isobutyl ester. The methyl ester and ethyl ester have proved particularly suitable.

The compounds of the formula (II) are obtainable from the parent acids in accordance with known processes (see, for example, J. Am. Chem. Soc. 72, 5139 (1950)).

To prepare the compounds according to the invention, of the formula (I), the compounds of the formula (II) are reacted with the compounds of the formula (III) in a molar ratio of 1:0.9 to 1:1.2, preferably 1:1 to 1:1.1.

Lewis acids which may be employed are aluminium chloride, aluminium bromide, iron-(III) chloride, antimony pentachloride, tin tetrachloride, boron trifluoride and other compounds known as Lewis acids. Preferably, aluminium chloride and tin tetrachloride are used. The Lewis acids are used in amounts of 1 to 5 mols, preferably 2 to 3 mols, per mol of acid halide.

The reaction according to the invention of the compounds (II) with the compounds (III) can be carried out with or without solvents. The use of a solvent is however advantageous, because it offers better temperature control and better homogenisation of the reaction mixture. Suitable solvents have proved to be chlorinated hydrocarbons, such as methylene chloride, ethylene chloride, carbon tetrachloride, tetrachloroethylene and dichlorobenzene, as well as carbon disulphide, nitrotoluene and nitrobenzene.

The reaction according to the invention is advantageously carried out at temperatures of 0° to 70° C., preferably 20° to 50° C.

The reaction according to the invention of the components (II) and (III) is advantageously carried out by mixing the catalyst with the solvent and adding the reactants individually or as a mixture. In the alkenedioic acid α,ω-dichlorides, α-chloride-ω-anhydrides or α-ester-ω-chlorides first formed when using α,ω-alkanedioic acid chlorides as component (II) and/or dimethylacrylic acid chloride or dimethylacrylic acid anhydride as component (III), the acid anhydride and acid chloride groups already undergo hydrolysis under the working-up conditions, so that after working up of the reaction mixtures, the corresponding α,ω-alkenedioic acids or α,ω-alkenedioic acid monoesters are obtained directly.

The 3-methyl-5-keto-α,ω-alkenedioic acids according to the invention, of the formula (I), are obtained as isomer mixtures, since the double bond is formed both in the 2-position and in the 3-position. For further conversion to the macrocyclic β-methyl-ketones, these isomer mixtures can be converted to the corresponding 3-methyl-5-keto-α,ω-alkanedioic acids directly, that is to say without separation into the isomers and without further purification, by hydrogenating them, for example in an alkaline medium, in the presence of customary hydrogenation catalysts, such as Raney nickel.

The 3-methyl-5-keto-α,ω-alkanedioic acids can subsequently be converted in various ways to the macrocyclic β-methyl-ketones, for example by reducing the keto group with hydrazine by the Wolff-Kischner method and cyclising the resulting 3-methyl-α,ω-alkanedioic acids by the process described by Ziegler et al. (Ann. 504, (1932), page 94) or the process described by Blomquist et al. (J. Am. Chem. Soc. 70, (1948), page 34), or alternatively—after protecting the keto group—in accordance with the process described by Mandapur (Tetrahedron 20, (1964), page 2601), namely by acyloin condensation and subsequent reduction of the macrocyclic acyloin.

The 3-methyl-5-keto-α,ω-alkenedioic acids according to the invention, of the formula (I), provide a new category of compounds which are obtained in a single step from easily accessible starting compounds, and by means of which 3-methyl-α,ω-alkanedioic acids and α,ω-alkanedioic acids, which contain a keto group in the β-position to a methyl group become easily accessible. The said α,ω-alkanedioic acids are important starting compounds for the preparation of macrocyclic β-methyl-ketones.

Macrocyclic β-methyl-ketones with 14 to 16 ring members, especially 3-methyl-cyclopentadecanone, known as d,l-muscone, are used extensively in perfumery and as important musk scents and fixatives. They can be prepared on an industrial scale by cyclising 3-methyl-α,ω-alkanedioic acids by the method of Ziegler (loc. cit.) or of Blomquist (loc. cit.), with loss of one carbon atom, or by subjecting α,ω-alkanedicarboxylic acids, which contain a keto group in the β-position to a methyl group, to acyloin condensation, with subsequent reduction, as described by Mandapur (loc. cit.). The said processes hitherto suffered from the disadvantage that the alkanedioic acids required for their implementation were only obtainable by multi-stage syntheses and were therefore only accessible with difficulty.

By means of the compounds according to the invention it becomes possible to prepare in an economical manner the 3-methyl-α,ω-alkanedioic acids and α,ω-alkanedioic acids which contain a keto group in the β-position to a methyl group, and hence also the macrocyclic β-methyl-ketones prepared, in turn, from these.

EXAMPLE 1

A mixture of 276.5 g (1 mol) of α,ω-dodecanedioic acid monoethyl ester chloride and 128 g (1 mol) of β,β-dimethylacrylic acid ethyl ester is added dropwise in the course of 1.5 hours to a suspension of 399 g (2.99 mols) of aluminium chloride in 300 ml of methylene chloride, at 30° to 35° C. After completion of the addition, the reaction mixture is heated for 3 hours at 45°–50° C. and is then hydrolysed with ice, after which the reaction product is extracted with methylene chloride. After distilling off the solvent, 370.4 g of crude product are obtained.

Separation of the reaction product by column chromatography over Kieselgel 60 (Merck) shows that the crude product contains 86% by weight of an isomer mixture of 3-methyl-5-keto-hexadecene-2-dioic acid diethyl ester, 3-methyl-5-keto-hexadecene-3-dioic acid diethyl ester and 3-methylene-5-keto-hexadecenedioic acid diethyl ester.

After repeated recrystallisation of the crude product from methanol, 191.1 g of 3-methyl-5-keto-hexadecene-2-dioic acid diethyl ester are obtained. Melting point: 58°–59° C.

EXAMPLE 2

A mixture of 140 g (0.5 mol) of α,ω-dodecanedioic acid dichloride and 134.4 g (1.05 mols) of β,β-dimethylacrylic acid ethyl ester is added dropwise to a suspension of 419 g (3.15 mols) of aluminium chloride and 140 g (0.5 mol) of α,ω-dodecanedioic acid dichloride in 300 ml of methylene chloride at 30° to 35° C. The reaction mixture is stirred for 3.5 hours at 45° to 50° C. and is then hydrolysed with ice water and extracted with methylene chloride. After stripping off the solvent, 376.6 g of crude product remain.

According to analysis by column chromatography, the crude product consists of 69% by weight of an isomer mixture of 3-methyl-5-keto-hexadecene-2-dioic acid 1-monoethyl ester, 3-methyl-5-keto-hexadecene-3-dioic acid 1-monoethyl ester and 3-methylene-5-keto-hexadecanedioic acid 1-monoethylester.

EXAMPLE 3

276.5 g (1 mol) of α,ω-dodecanedioic acid monoethyl ester chloride and 156 (1 mol) of β,β-dimethylacrylic acid n-butyl ester are reacted as described in Example 1. 405 g of crude product are obtained.

Separation of the crude product by means of column chromatography over Kieselgel 60 (Merck) shows that the product contains 82% by weight of an isomer mixture of 3-methyl-5-keto-hexadecene-2-dioic acid α-n-butyl-ω-ethyl ester, 3-methyl-5-keto-hexadecene-3-dioic acid α-n-butyl-ω-ethyl ester and 3-methylene-5-keto-hexadecane-dioic acid α-n-butyl-ω-ethyl ester.

EXAMPLE 4

130 g (0.5 mol) of α,ω-undecanedioic acid monoethyl ester chloride and 64 g (0.5 mol) of 62 ,β-dimethylacrylic acid ethyl ester are reacted as described in Example 1. 170 g of crude product are obtained.

Separation of the crude product by means of column chromatography over Kieselgel 60 (Merck) shows that the crude product contains 84% by weight of an isomer mixture of 3-methyl-5-keto-pentadecene-2-dioic acid diethyl ester, 3-methyl-5-keto-pentadecene-3-dioic acid diethyl ester and 3-methylene-5-keto-pentadecanedioic acid diethyl ester.

EXAMPLE 5

(a) 150 g (0.41 mol) of 3-methyl-5-keto-hexadecene-2-α,ω-dioic diethyl ester (melting point: 58°–59° C.; prepared according to Example 1) are mixed with a solution of 50 g (0.9 mol) of potassium hydroxide in 240 ml of water and 500 ml of ethanol, and are hydrogenated, after adding 16 g of Raney nickel, at 40° C. and 40 atmospheres hydrogen pressure. The hydrogen absorption is 100% of theory.

After filtering off the catalyst, the solution is concentrated and acidified with hydrochloric acid, and the reaction product is extracted with ethyl acetate.

125.5 g (98% of theory) of 3-methyl-5-keto-hexadecanedioic acid are obtained. Melting point: 84°–85° C.

(b) 35 g (0.11 mol) of 3-methyl-5-keto-hexadecanedioic acid (obtained as described under (a) above), 30.8 g (0.55 mol) of potassium hydroxide, 150 ml of diethylene glycol and 20.6 g (0.33 mol) of 80% strength hydrazine hydrate are heated to the reflux temperature for 2 hours. Water and excess hydrazine are then distilled off and the residue is heated for one hour at 220° C. When it has cooled to 15° C., the reaction mixture is acidified with hydrochloric acid and extracted with ethyl acetate. The residue which remains after removing the ethyl acetate from the organic phase is recrystallized from petroleum ether. 30.3 g (91% of theory) of 3-methyl-hexadecanedioic acid are obtained. Melting point: 77°–78° C.

The yield of 3-methyl-hexadecanedioic acid, relative to 3-methyl-5-keto-hexadecene-2-α,ω-dioic acid diethyl ester, is 89% of theory.

If instead of crystalline 3-methyl-5-keto-hexadecene-2-dioic acid diethyl ester, the crude product of Example 1, obtained after distilling off the solvent, is employed in reductions (a) and (b) described above, 3-methyl-hexadecanedioic acid is obtained in a yield of 62% of theory, relative to crude product employed.

EXAMPLE 6

(a) 150 g (0.41 mol) of 3-methyl-5-keto-hexadecene-2-dioic acid diethyl ester (melting point: 58°–59° C.; obtained according to Example 1) are dissolved in 1,000 ml of methanol and are hydrogenated, after adding 16 g of Raney nickel, at 20° C. and 40 atmospheres hydrogen pressure. The hydrogen absorption is virtually 100% of theory. After filtering off the catalyst, the solvent is stripped off.

148 g of 3-methyl-5-keto-hexadecane-α,ω-dioic acid diethyl ester are obtained. Melting point: 25° C.

(b) 148 g (0.4 mol) of 3-methyl-5-keto-hexadecane-α,ω-dioic acid diethyl ester (obtained as described under (a) above) are reduced with 2 mols of potassium hydroxide and 1.2 mols of hydrazine hydrate as described in Example 5(b).

108 g (=90% of theory) of 3-methyl-hexadecenedioic acid are obtained. Melting point: 77° C.

The yield of 3-methyl-hexadecanedioic acid, relative to 3-methyl-5-keto-hexadecene-2-dioic acid ethyl ester, is 90% of theory.

EXAMPLE 7

300 g of the crude product obtained according to Example 2 are hydrogenated under the conditions described in Example 5(a) and then reduced, without further purification, under the conditions described in Example 5(b).

140 g (56% of theory, relative to crude product employed) of 3-methyl-hexadecane-α,ω-dioic acid are obtained.

What is claimed is:

1. A 5-keto-α,ω-alkenedioic acid or ester of the formula

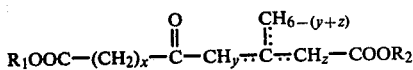

where
a double bond is in one of the positions indicated by the broken lines,
$R_1$ and $R_2$ each independently is a hydrogen atom or a $C_1$-$C_4$-alkyl group,
x is 9, 10 or 11, and
one of y and z is 2 and the other is 1 or 2.

2. A compound according to claim 1, wherein $R_1$ and $R_2$ each independently is a hydrogen atom, or a methyl or ethyl group.

* * * * *

UNITED STATES PATENT AND TRADEMARK OFFICE
CERTIFICATE OF CORRECTION

PATENT NO. : 4,259,518
DATED : Mar. 31, 1981
INVENTOR(S) : Kurt Bauer et al

It is certified that error appears in the above—identified patent and that said Letters Patent is hereby corrected as shown below:

Title Page, "Bayer Aktiengesellschaft, Leverkusen, Germany"
Assignee should be "Haarman & Reimer GMBH, Holzminden, Germany.

*Signed and Sealed this*

*First* Day of *December 1981*

[SEAL]

Attest:

GERALD J. MOSSINGHOFF

*Attesting Officer*     *Commissioner of Patents and Trademarks*